(12) United States Patent
Abraham et al.

(10) Patent No.: US 6,717,667 B2
(45) Date of Patent: Apr. 6, 2004

(54) OPTICAL FOOD OIL QUALITY SENSOR

(75) Inventors: Varghese Abraham, Brampton (CA); Sajeev John, London (CA); Puthenveetil John, London (CA)

(73) Assignee: Northern Photonics, London (CA)

( * ) Notice: Subject to any disclaimer, the term of this patent is extended or adjusted under 35 U.S.C. 154(b) by 0 days.

(21) Appl. No.: 10/340,843

(22) Filed: Jan. 13, 2003

(65) Prior Publication Data

US 2003/0147073 A1 Aug. 7, 2003

Related U.S. Application Data

(63) Continuation of application No. PCT/CA01/01008, filed on Jul. 12, 2001.
(60) Provisional application No. 60/217,723, filed on Jul. 12, 2000.

(51) Int. Cl.[7] .......................... G01N 33/03; G01N 21/64
(52) U.S. Cl. ................. 356/318; 356/417; 250/458.1
(58) Field of Search ................. 356/317, 318, 356/417; 250/458.1, 459.1, 461.1, 461.2

(56) References Cited

U.S. PATENT DOCUMENTS 5,472,878 A * 12/1995 Lewis et al. ................ 436/61
5,656,810 A * 8/1997 Alfano et al. ............... 250/301

OTHER PUBLICATIONS

Engelsen: "Explorative Spectrometric Evaluations of Frying Oil Deterioration" Journal of the American Oil Chemists' Society, vol. 74, No. 12, Dec. 1997, pp. 1495–1508.*

* cited by examiner

Primary Examiner—F. L. Evans
(74) Attorney, Agent, or Firm—Fasken Martineau DuMoulin LLP; Neil Henderson

(57) ABSTRACT

An instrument for measuring reliably and instantaneously the chemical quality of cooking oil, and for distinguishing between color changes due to chemical changes and color changes due to the presence of minute size food particles in various oils.

20 Claims, 19 Drawing Sheets

EXPERIMENTAL SETUP

LASER SENSOR OPTICS MODULE: INTERIOR VIEW

EXTERIOR VIEW: OPTICS & DISPLAY MODULES

OPTICAL FOOD OIL QUALITY SENSOR

This application is a Continuation Application from PCT Application Ser. No. PCT/CA01/01008, filed Jul. 12, 2001, which claims priority from U.S. application Ser. No. 60/217,723, filed Jul. 12, 2000.

BACKGROUND OF THE INVENTION

Fast food restaurants use both vegetable shortenings and animal fats for frying purposes. Since this operation is carried out at high temperatures in the presence of water and starch, several chemical changes take place in the oil, degrading the oil quality. Heretofore, there has been no systematic or accurate way of monitoring oil quality in restaurants quickly and easily as the oil is repeatedly used in frying. The restaurant manager's decision to change or not to change the oil is typically based on a visual inspection of the colour of the oil. The appearance of used cooking oil to the naked eye is the result of light which is both scattered and absorbed by the oil. For example, bad oil appears dark because of chemical changes that cause light absorption. Good oil may also appear dark if there are particle impurities which have sizes comparable to the wavelength of light or higher (larger than about 0.3 microns). This can create a situation where bad oil is repeatedly used at the expense of the consumer's health. Conversely, oil may be prematurely changed, to the needless expense of the restaurant owner.

SUMMARY OF THE INVENTION

The present invention seeks to provide instrumentation which measures reliably and instantaneously the chemical quality of cooking oil. It can also distinguish between colour changes due to chemical changes and colour changes due to the presence of minute size food particles in various oils.

Another object of the present invention is to provide an apparatus suitable for use in restaurants, homes and other businesses for the regular monitoring of the cooking oil which is safe, user friendly and inexpensive.

In furtherance of at least some of the foregoing objects, the applicant has appreciated that the following scientific and technical conclusions may be drawn from experimental studies of cooking oil samples as disclosed hereinafter:

(i) There is on average a clear correlation between laser induced fluorescence and the concentration of polar compound and in the oil.

(ii) Data for fluorescence vs. polar compound concentration exhibits significant standard deviation from the average. This strongly suggests that fluorescence is a measure of a variety of different chemical changes in the cooking oil of which polar compound concentration is a major component. For example, a large fluorescence signal is observed if either the polar compound concentration or the percentage of Free Fatty Acids is high. This indicates that fluorescence must be regarded as a composite index for oil quality and is not limited to a single chemical change.

(iii) Each curve shows a "knee" when the polar compound concentration reaches approximately 25%. Below this knee, the fluorescence increases slowly with polar compound concentration (with significant fluctuations) and the oil is reusable. Above this knee, the fluorescence increases extremely rapidly with polar compound concentration and reuse of the oil is ill-advised. The existence of this knee in our regression curves plays a key role in the ability of an oil sensor to discriminate between usable and non-reusable oil.

BRIEF DESCRIPTION OF THE FIGURES

FIG. 10b illustrates schematically an exterior view of optical sensor shown in FIG. 10a;

In FIG. 12c standard deviation about the average value is depicted as a vertical bar;

In FIG. 12e standard deviation about the average is indicated as a vertical bar;

DETAILED DESCRIPTION

Figure 1:
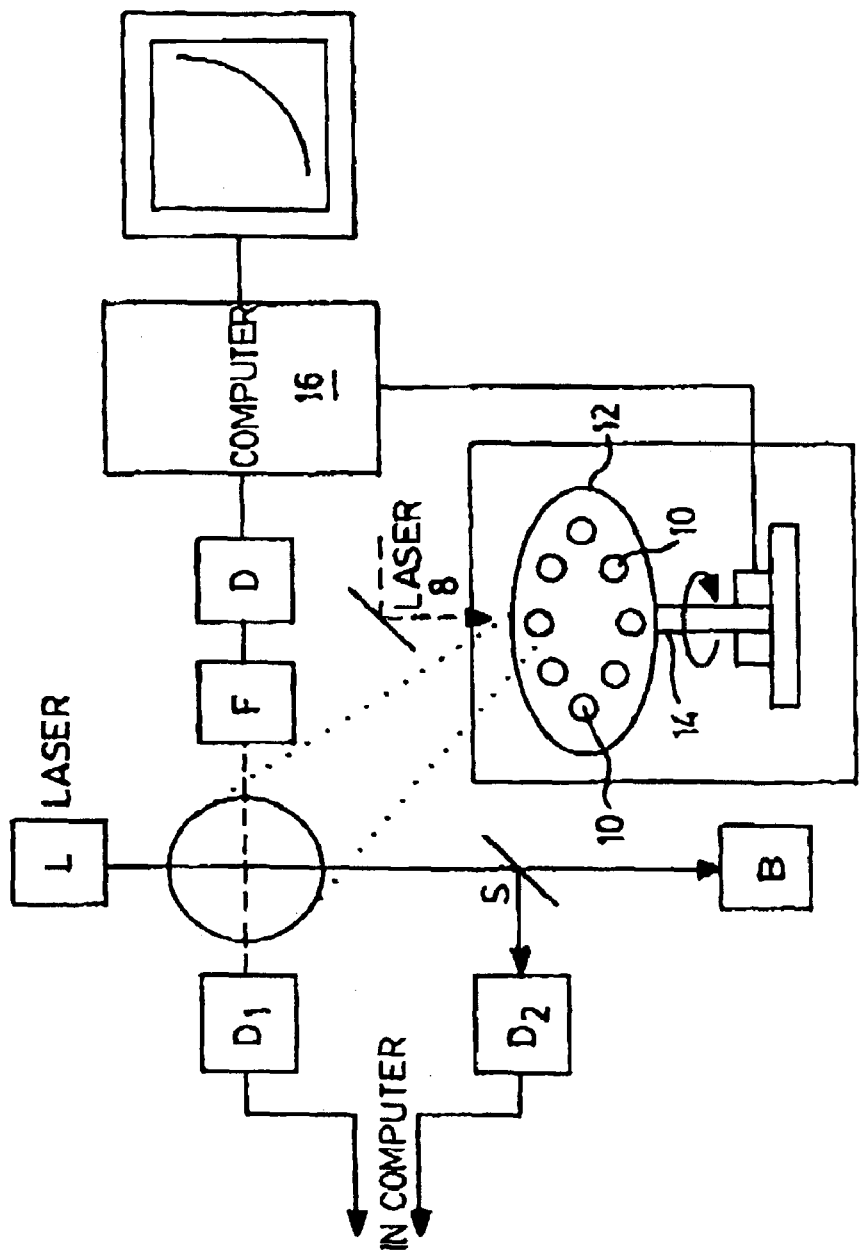
FIG. 1 shows schematically an experimental model using oil apparatus for monitoring cooking oil quality in accordance with the present invention.

When light passes through cooking oil, absorption and scattering reduce the amount of light that is transmitted through the sample. This scattering takes two forms. The first is elastic scattering in which the scattered light has the same frequency as the incident light. The second is inelastically scattered light, in the form of fluorescence emission. This inelastic or fluorescent scattering results in light which has a lower frequency than the incident light.

The applicant has recognized fluorescent laser light scattering signal is independent of food particles and other impurities which may enter the oil in the process of cooking. Rather, impurity particles, which can be removed from the oil by oil filtration, are detected by means of elastic light scattering.

If light from a laser is used, it is possible to separate the inelastically scattered fluorescent light from the elastically scattered light. By passing the total scattered light (i.e. a mixture of the elastically and inelastically scattered light) through an optical cutoff filter, it is possible to remove the elastically scattered component and measure only the fluorescence, As a result, it is possible to determine the chemical quality of cooking oil even prior to oil filtration.

With the present invention, a device based on the foregoing principles is able to accurately provide an indication whether to continue using a given volume of cooking oil, whether to filter and then re-use the oil, or whether to simply discard the oil. In particular, by separating the elastically scattered light from the fluorescence, the present invention can instantaneously measure both the amount of filterable impurities and the percentage of degraded oil molecules.

The absorption and subsequent fluorescent emission of light by oil molecules is a consequence of the detailed rotational-vibrational and electronic excitation spectrum of these molecules. This in turn is controlled by chemical and structural changes in the oil molecule. These changes include increase in polarity, formation of free fatty acids, and oxidation of the fatty acids. In particular, in unused oil, there is little or no fluorescence in the visible spectrum and the oil is relatively colourless. As the oil is used under normal cooking conditions over an extended period of time, the first excited electronic, ro-vibrational band of the oil molecules moves down in frequency. As the bottom of this excited band moves through the visible range, the oil acquires a reddish tinge when illuminated with white light.

Laser light scattering provides an accurate spectroscopic fingerprint of the structural and chemical changes in the oil molecule. From this it is possible to instantaneously infer the percentage of free fatty acids and polar molecules in the oil on average, given a detailed mapping between chemical properties of the used cooking oil to the optical scattering properties.

(a) Experiments and Measurements

Experiments to study the interaction of light with used cooking oil were initiated using laser light of various frequencies. Three different lasers of wavelengths 670 nm, 633 nm, 544 nm were used in the early investigations. Total scattered light, fluorescent scattered light, and optical attenuation were all measured. The optical data was then correlated with the supplied chemical data.

Lasers used were He—Ne gas lasers for 544 nm and 633 nm wave lengths. For the 670 nm wavelength, a semiconductor diode laser was used. Laser power ranged from 5 mW to 1 mW.

The oil samples measured were collected from McDonald's™ restaurants at various times of the year as sets of three. Each set consisted of oil samples from three different stores for each of four foods: french fries, filet, nuggets and chicken. For each food oil used there were eight samples covering eight consecutive days.

FIG. 1 shows the experimental set up for the optical measurements. Laser light from a laser 8 is incident on an oil sample 10 held in a sample holder 12 consisting of a 1" diameter glass tube. Part of the transmitted light is directed by a beam splitter (S) on to a photo detector (D2) which measures the absorption coefficient of the oil 10. The rest of the transmitted light is absorbed in a beam dump (B). Two detectors D1, D2 are positioned at right angles to the laser beam. The detector to the left (D1) measures the total light scattered at 90 degrees. The detector to the right (D2) collects the scattered light that is passed through an optical filter (F). The optical filter (F) has the property that it cuts off light at the laser frequency and transmits only the lower frequency (fluorescent) light. Thus detector D2 measures the fluorescent scattered light at 90 degrees.

Figure 2:
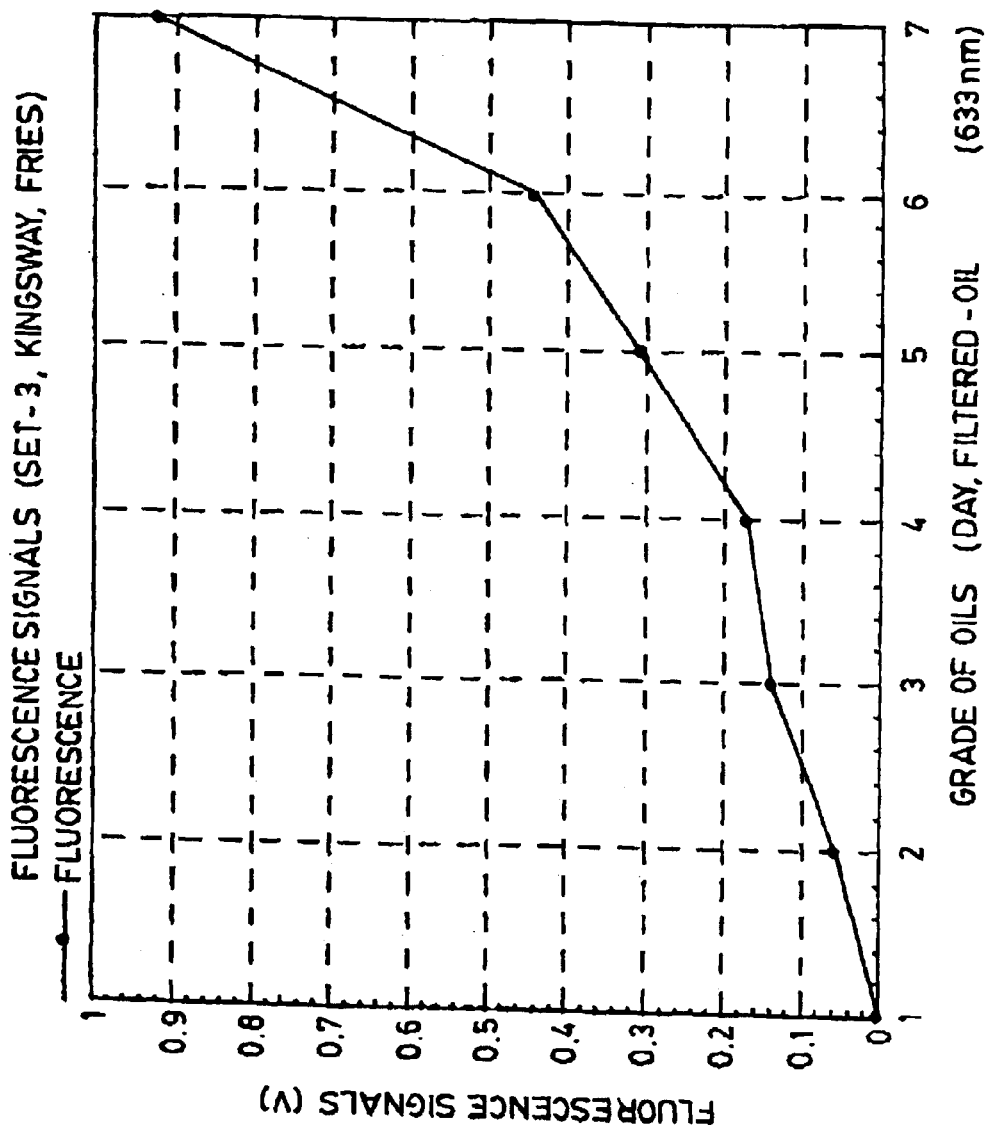
FIG. 2 illustrates graphically data for fluorescent light scattering as a function of oil usage over time (fries)
Figure 3:
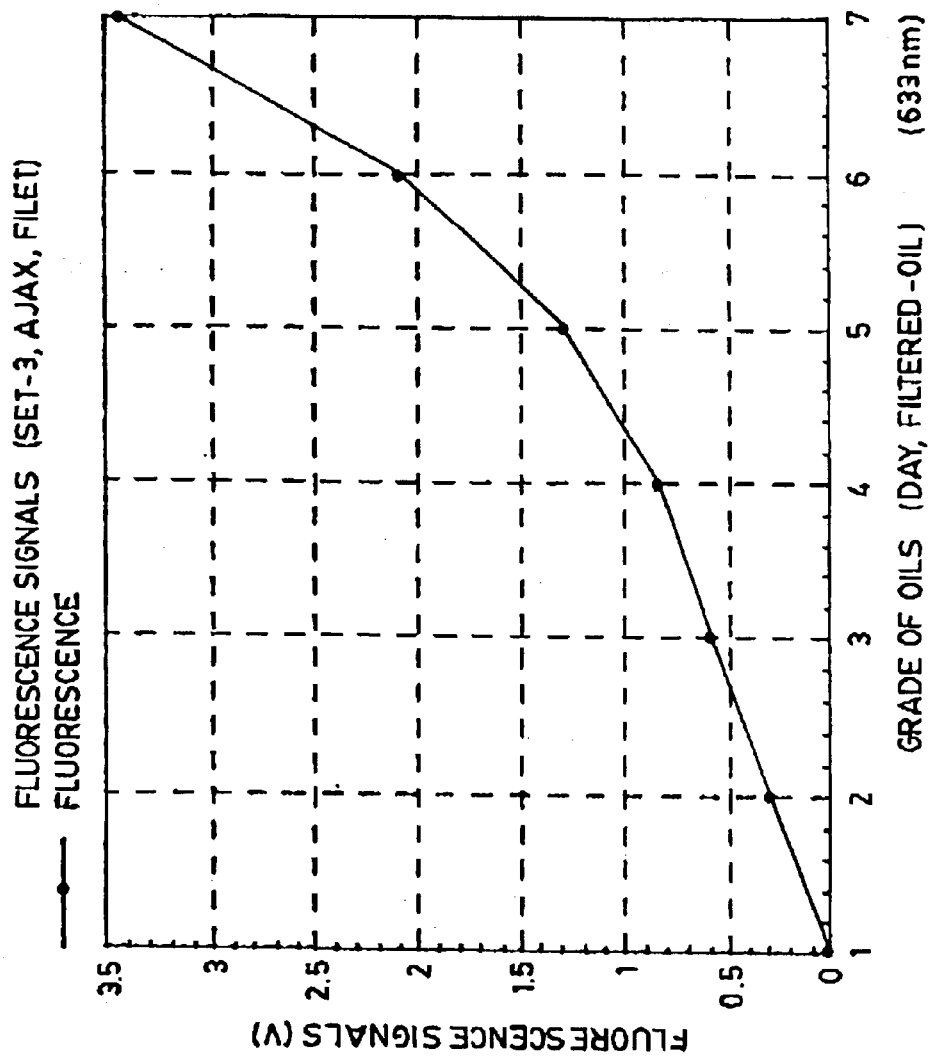
FIG. 3 illustrates graphically data for fluorescent light scattering as a function of oil usage over time (meat)
Figure 4:
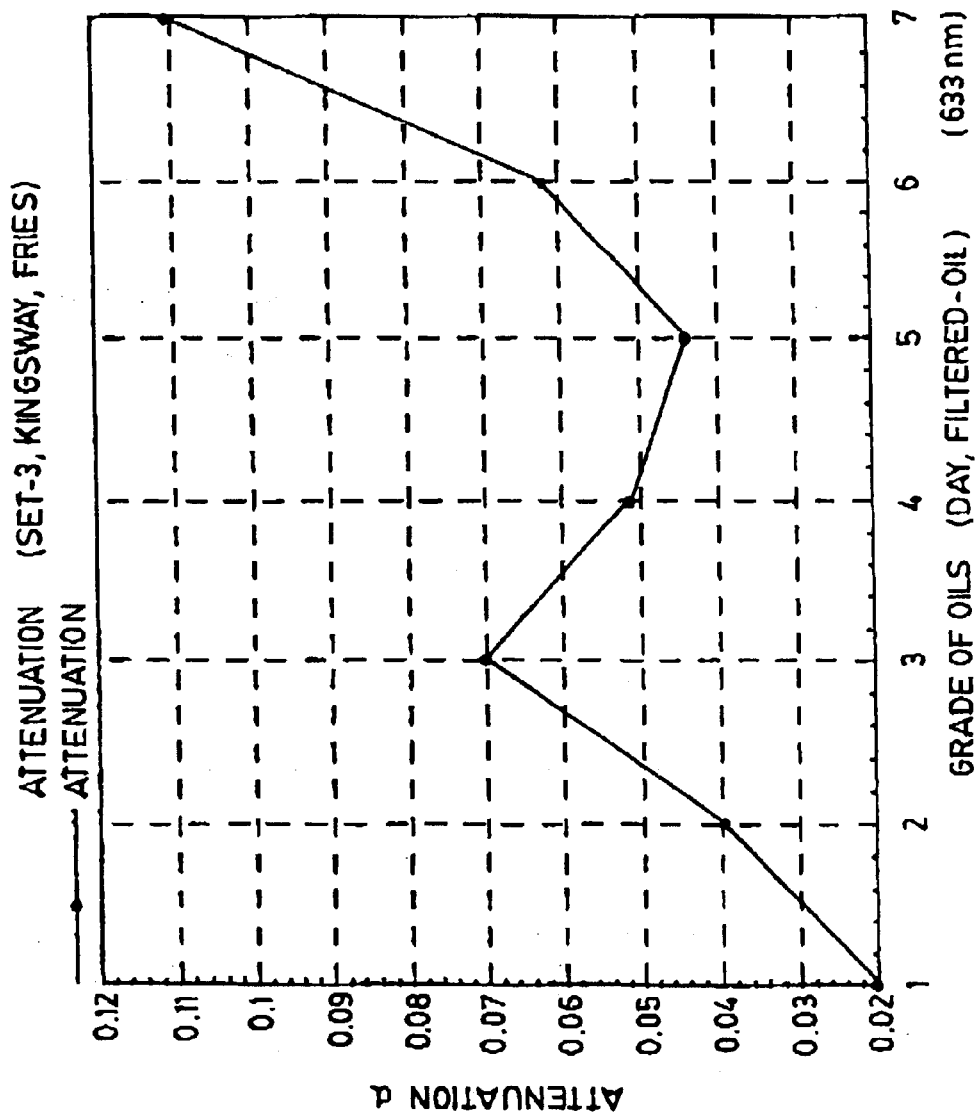
FIG. 4 illustrates graphically data for total light scattering (attenuation) as a function of oil usage over time. The data shown includes the combined effect of fluorescent light scattering due to chemical degradation of oil and elastic light scattering due to small food particle impurities.
Figure 5A:
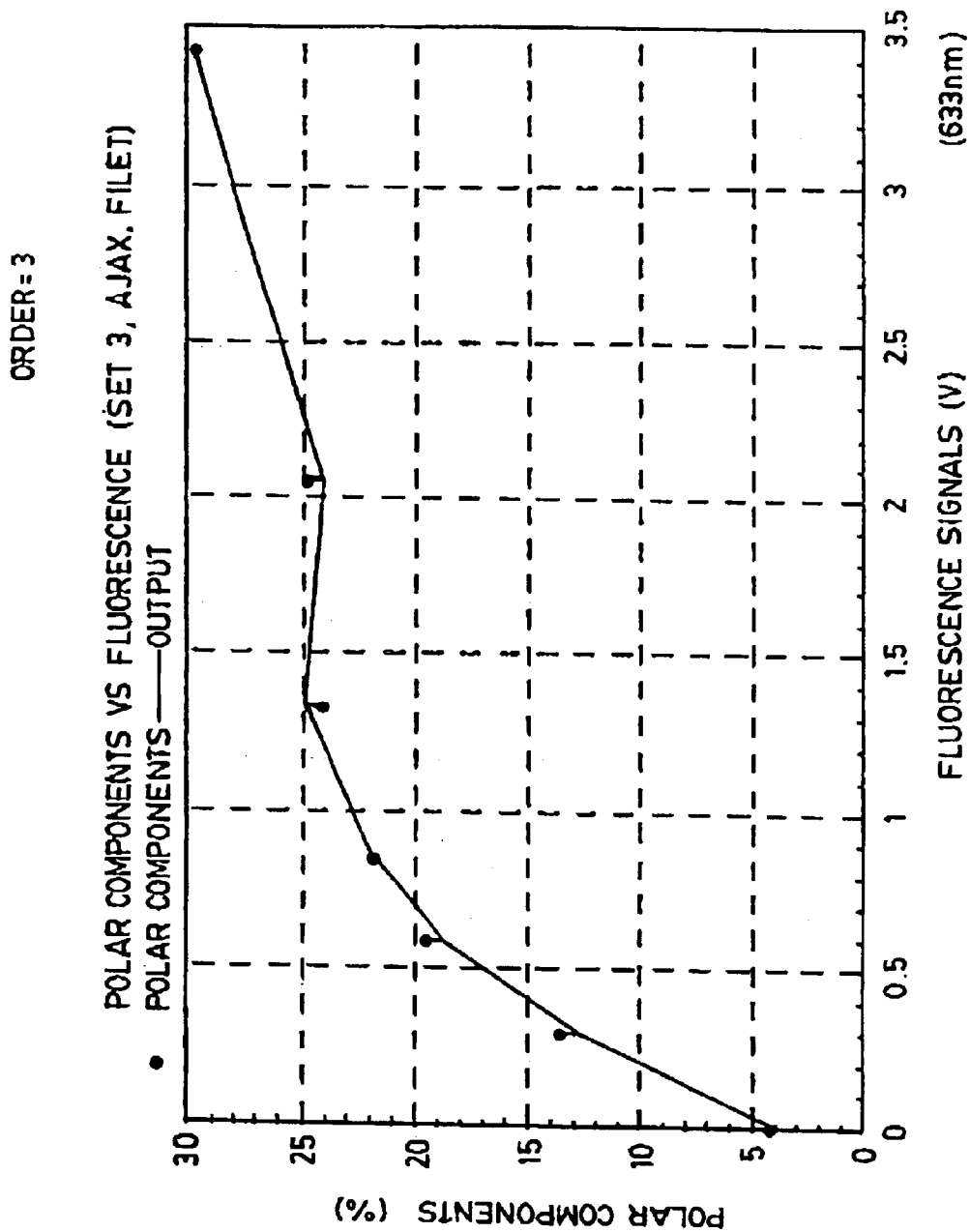
FIG. 5a illustrates graphically correlation between fluorescence and polar compound chemical data in the form of a regression curve (meat)
Figure 5B:
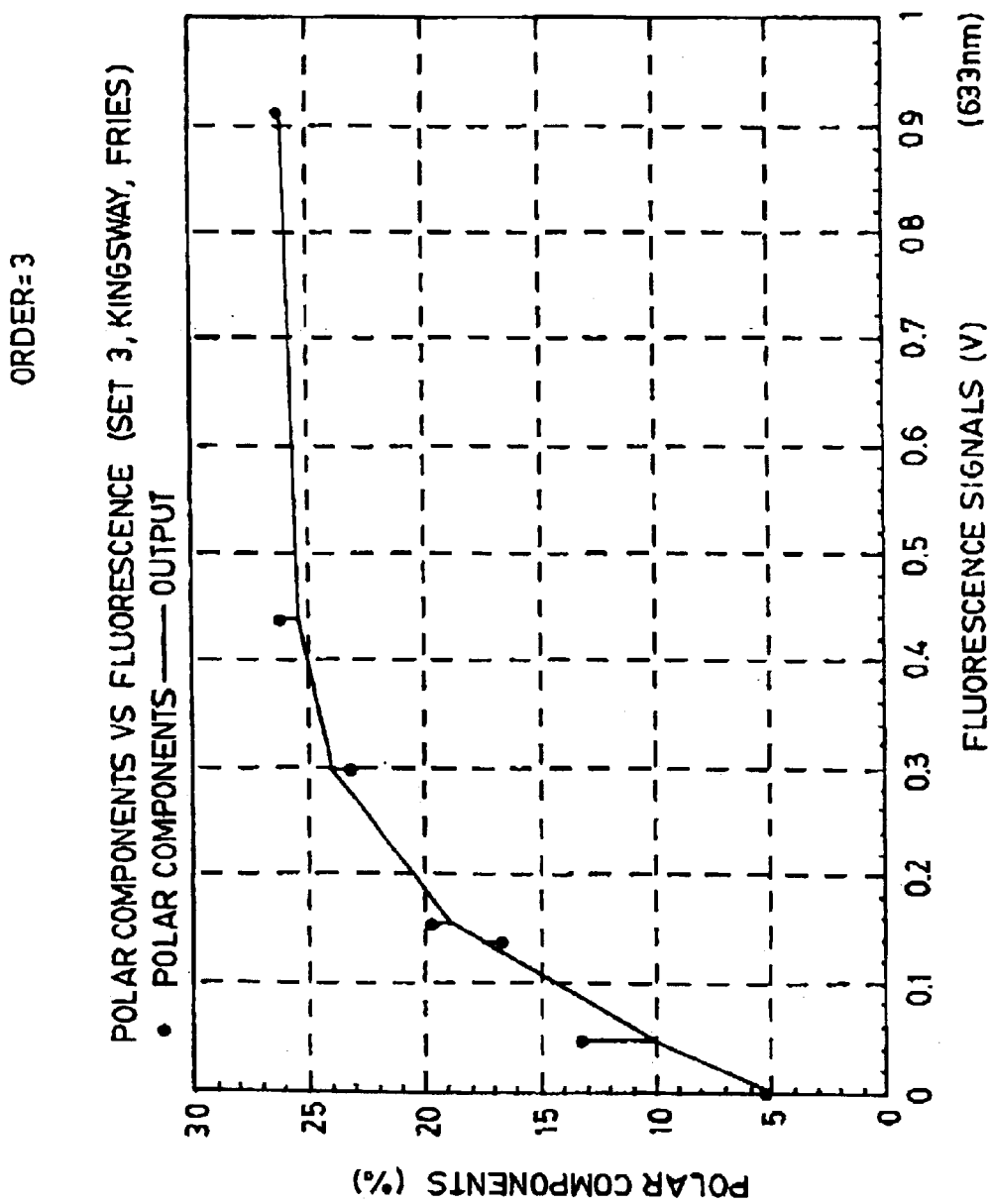
FIG. 5b illustrates graphically the correlation between fluorescence and polar compound chemical data in the form of a regression curve (fries)

FIGS. 2 to 4 show graphically the typical data for total scattering, fluorescence and attenuation. These graphs are drawn in Stanford Graphics scientific software which was used in analysis of the data and correlation with chemical data. Shown also in FIGS. 5a and 5b are graphs illustrating the typical correlation between fluorescence and polar compound chemical data, in the form of a regression curve.

Figure 6:
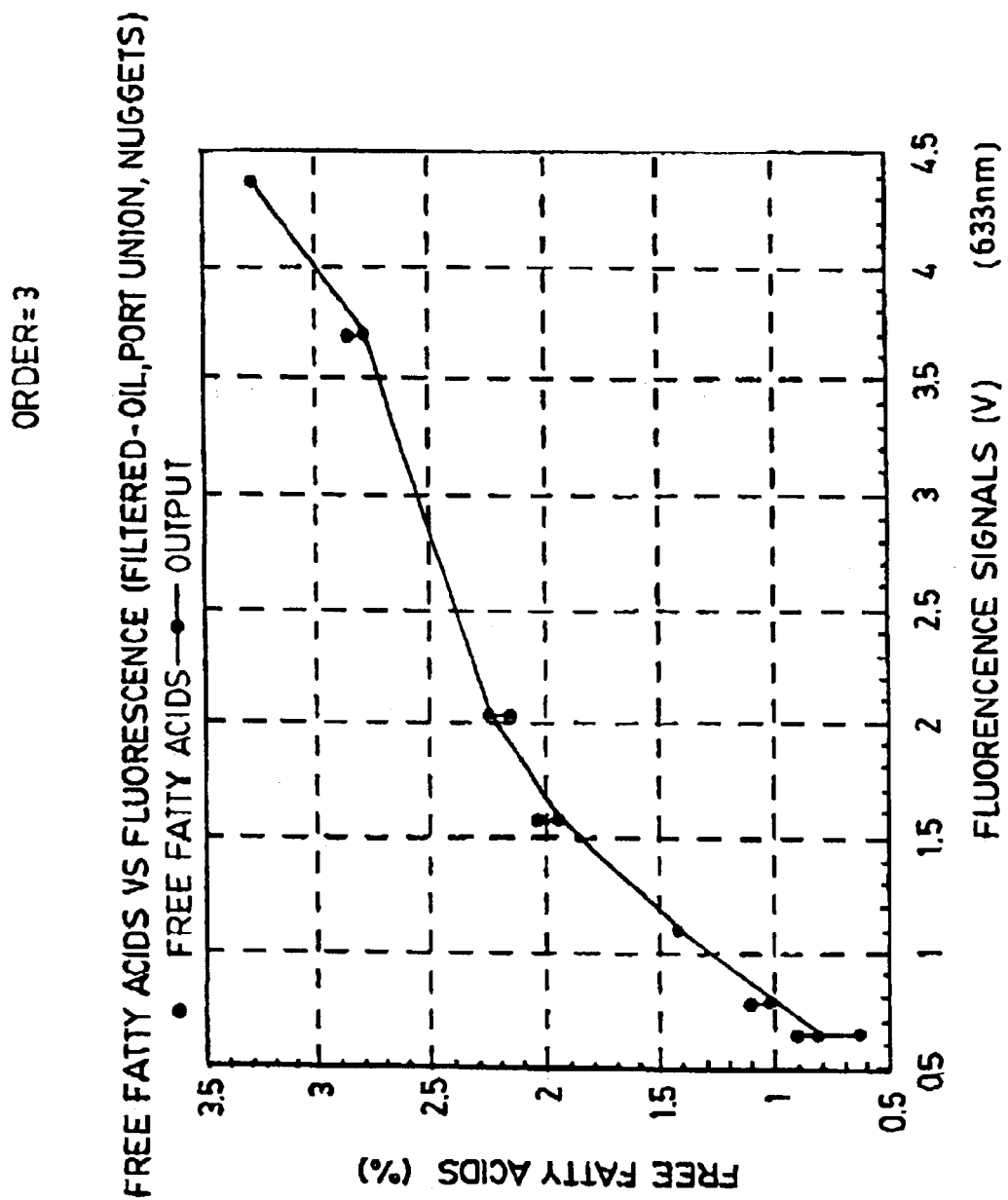
FIG. 6 illustrates a regression curve showing the correlation between fluorescence and changes in fatty acid concentration.
Figure 7:
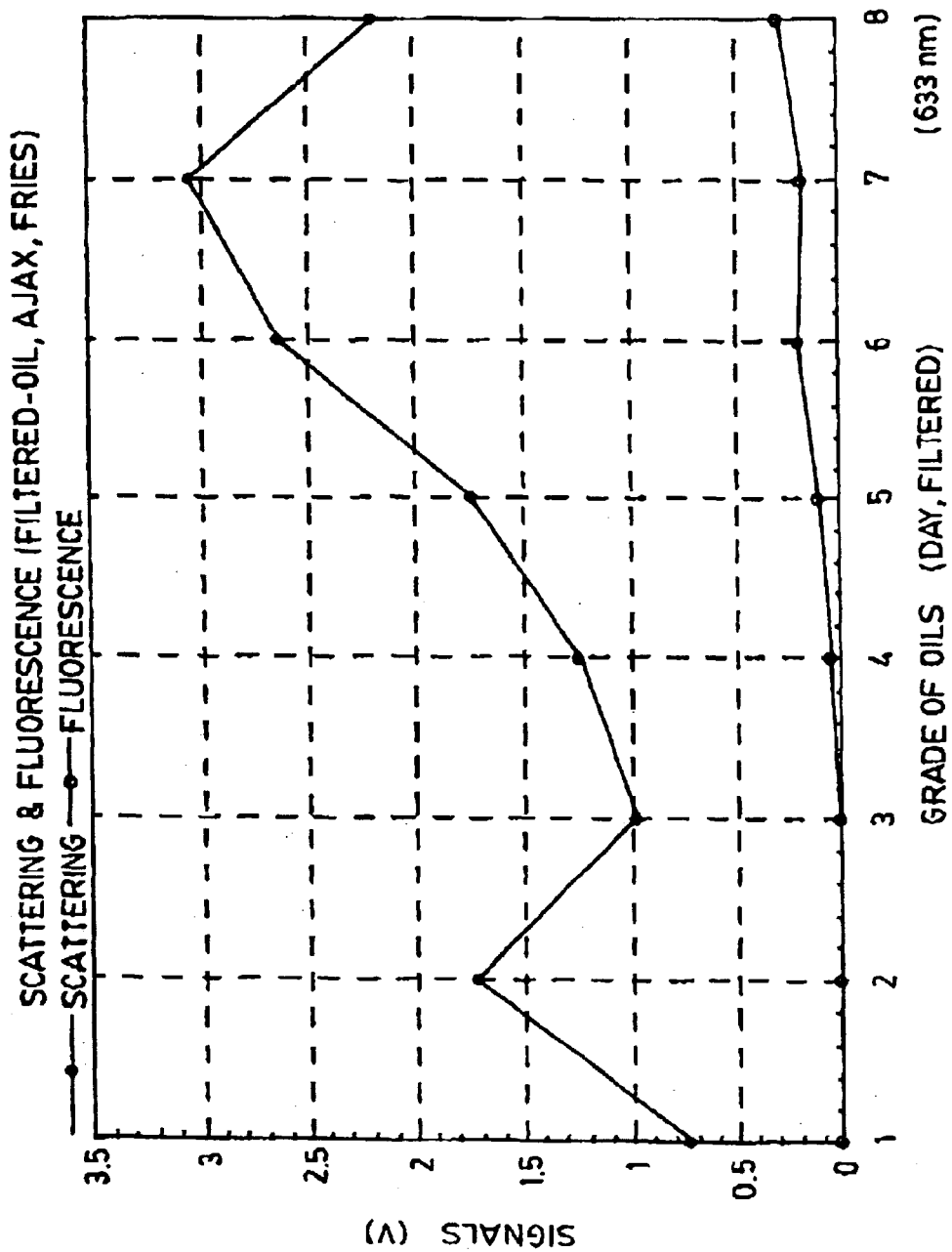
FIG. 7 illustrates graphically the comparison between fluorescent and total scattering.

FIG. 6 shows a typical regression curve of the correlation between fluorescence and changes in fatty acid concentration. It is clear that there is strong correlation between fluorescence and chemical changes. FIG. 7 illustrates a comparison between fluorescence and total scattering, indicating that the intensity and shape of the two are different. Similar measurements were conducted on the eight samples 10 of each food obtained at each store in the three sets. As a result, it was concluded that there is a useful correlation on average between chemical changes in oil and the corresponding changes in the intensity of the fluorescent signals.

Figure 8:
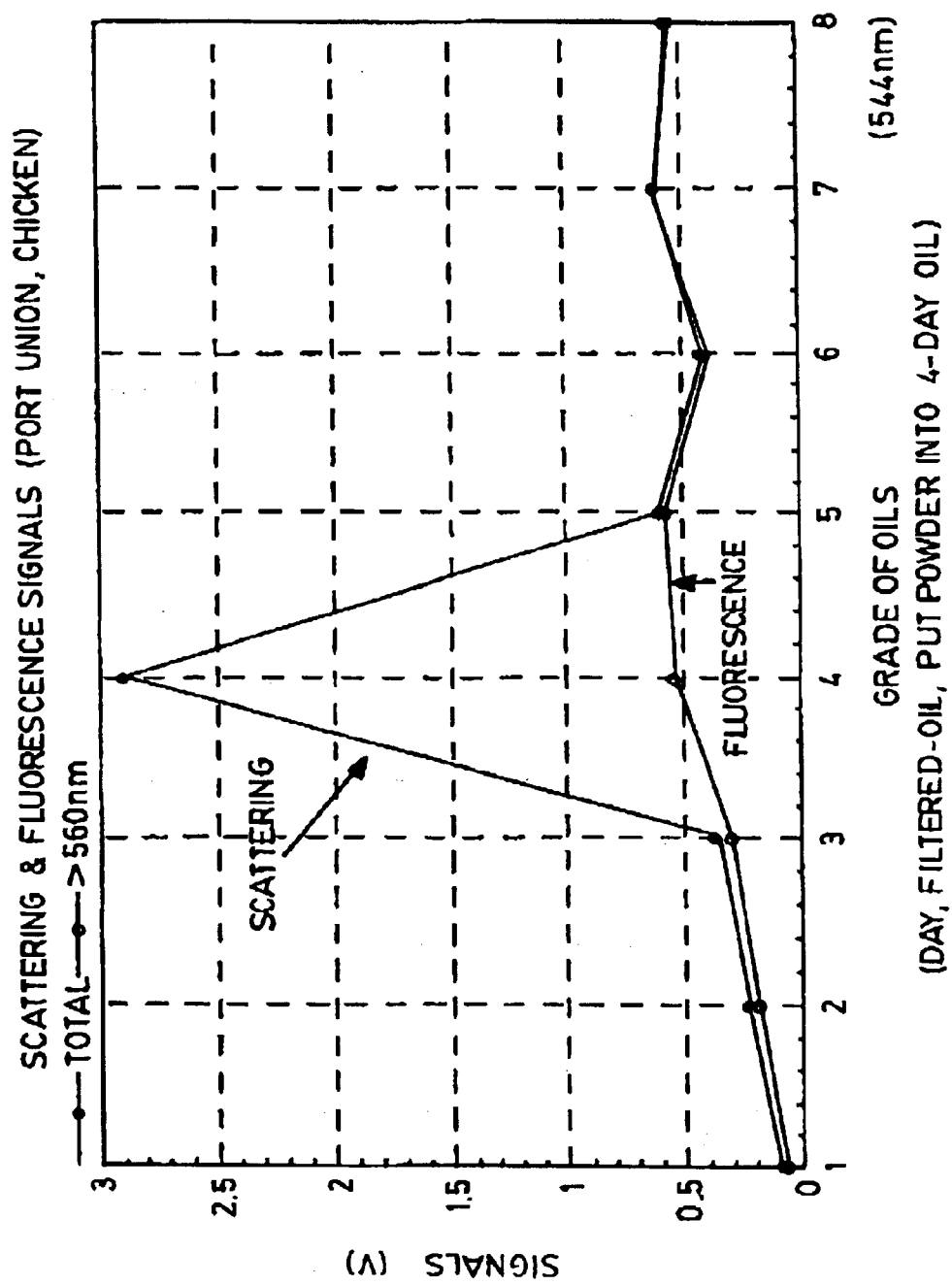
FIG. 8 illustrates graphically the relationship between fluorescence and fluorescent emission is not affected by the presence of tiny solid particles which elastically scatter light and which affect the visual appearance of the oil.

The fact that fluorescent emission is not affected by the presence of tiny solid or food particles in the oil was verified by intentionally adding solid particles to the oil. This is best shown in FIG. 8, where fine solid particle impurities were added to the four day old oil. While the total scattered light intensity is significantly increased by the presence of solid particles in the four day old oil, the fluorescence intensity remains unaffected.

Figure 9:
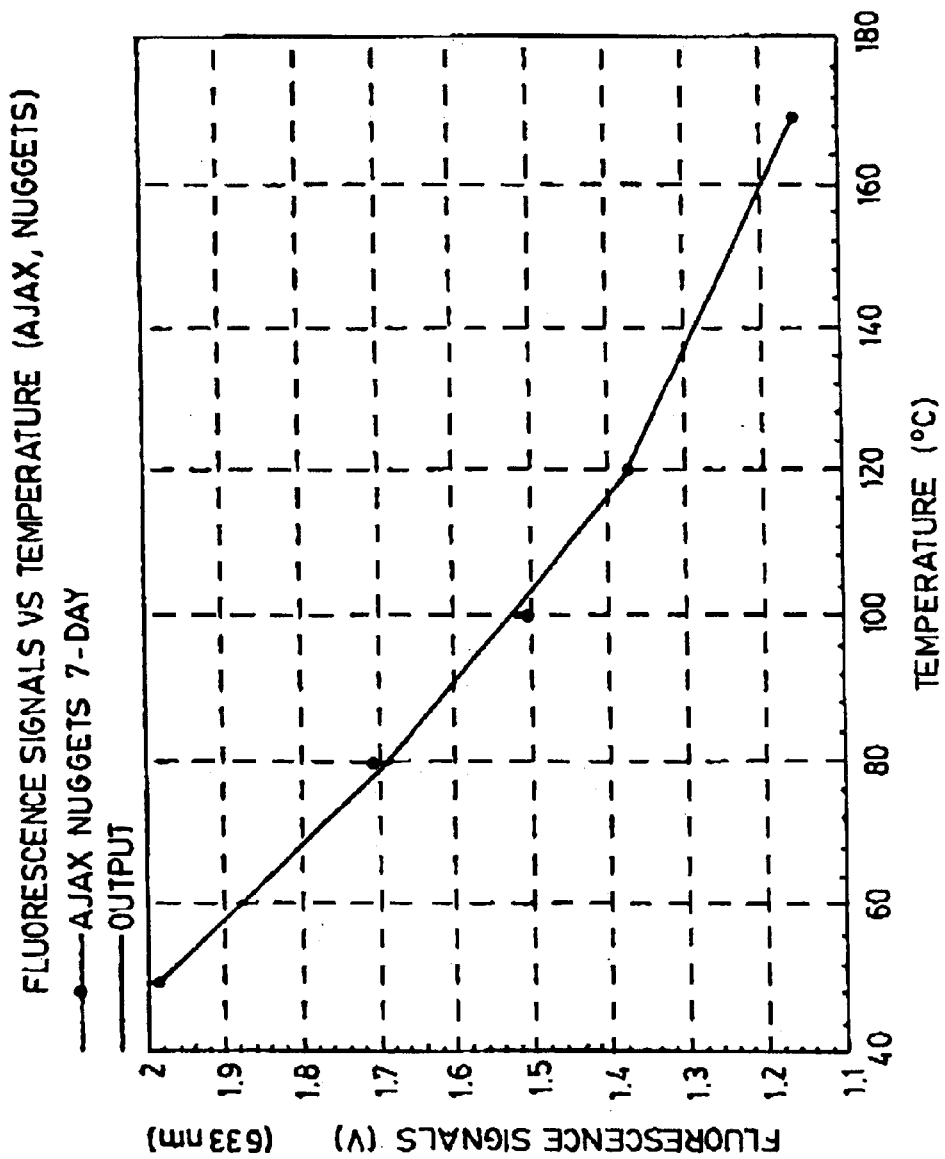
FIG. 9 illustrates graphically the relationship between fluorescence and oil temperature.

The above measurements were conducted at an oil temperature of 50 C. Measurements were also carried out to determine variations in fluorescent emission as a function of temperature. It was observed that the fluorescent intensity is higher at lower temperatures. This is advantageous because if the oil has to be handled during measurements, it can be done so most efficiently at a safe handling temperature. Measurements were carried out with a representative number of samples to determine how the fluorescent signal is affected by changes in the temperature of the oil at the time of measurement. A typical graph is shown in FIG. 9 for a range of temperatures from 50 C. to 170 C. showing an increase in the fluorescent signal as the temperature is lowered. Studies suggest that 50–60 degrees C. is the ideal temperature from the standpoint of safety and measurement sensitivity, with an optimal temperature in terms of oil freezing, stability and safety at close to 60 C. for the measurements. At this temperature, the fluorescent signal is stable with respect to small variations of temperature within about 5 degrees. The experimental investigations, in addition to establishing the scientific feasibility of using light scattering to monitor oil quality, also enable a determination of optimum conditions for device development.

(b) Final Sample Testing and Analysis

For final sample testing, a red diode laser was the laser of choice for a prototype system because of size, cost and wavelength, and readily available red diode lasers of wavelengths 635 nm and 670 nm were used.

Based on all data collected, it was observed that oil from french fries has a different characteristic behaviour from that of nuggets, fillet, and chicken. As such, the invention most preferably has at least two separate settings in order to determine oil quality for two, three, four or more distinct foods. Accordingly, in a preferred embodiment a selector switch is installed to switch the operation of the device from at least between french fries and the other meat products. In general, the device requires separate calibration for different oil types, compositions and cooking conditions which may vary from industry to industry.

Data for fluorescence vs. polar compound concentration exhibited significant standard deviation from the average. This strongly suggests that fluorescence is a measure of a variety of different chemical changes in the cooking oil of which polar compound concentration is a major component. For example, a large fluorescence signal is observed if either the polar compound concentration or the percentage of free fatty acids is high. This suggests that fluorescence must be regarded as a composite index for oil quality and is not limited to a single chemical change. The device is not a substitute for a polar component meter. However, under normal cooking conditions, it can be effectively used to infer oil quality of which polar components are a major factor.

The regression curve of chemical changes (as measured by polar compounds and free fatty acids) is a nonlinear function of fluorescent light scattering. In particular, the fluorescent light scattering increases much more rapidly in the late stage of the oil cycle. In other words, laser light scattering provides a highly sensitive probe of oil quality near the time when a decision must be made whether the oil should be re-used or discarded under normal cooking conditions. We have arrived at the following conclusions based on measurements on a statistically significant number of oil samples collected from a wide distribution of stores over an extended period of time:

(a) There is on average a clear correlation between laser induced fluorescence and the concentration of polar compounds in the oil. For each of the foods tested so, there is a characteristic curve relating the fluorescent light intensity (measured as a voltage by our optical detector) to the polar compound concentration. Each curve shows a "knee" when the polar compound concentration reaches approximately 25%. Below this knee the fluorescence increases slowly with polar compound concentration (with significant fluctuations) and the oil is reusable. Above this knee, the fluorescence increases extremely rapidly with polar compound concentration.

(b) The oil from french fries shows a different fluorescence characteristic behaviour from that of nuggets, fillet, and chicken.

(c) Prototype Device

Figure 10A:
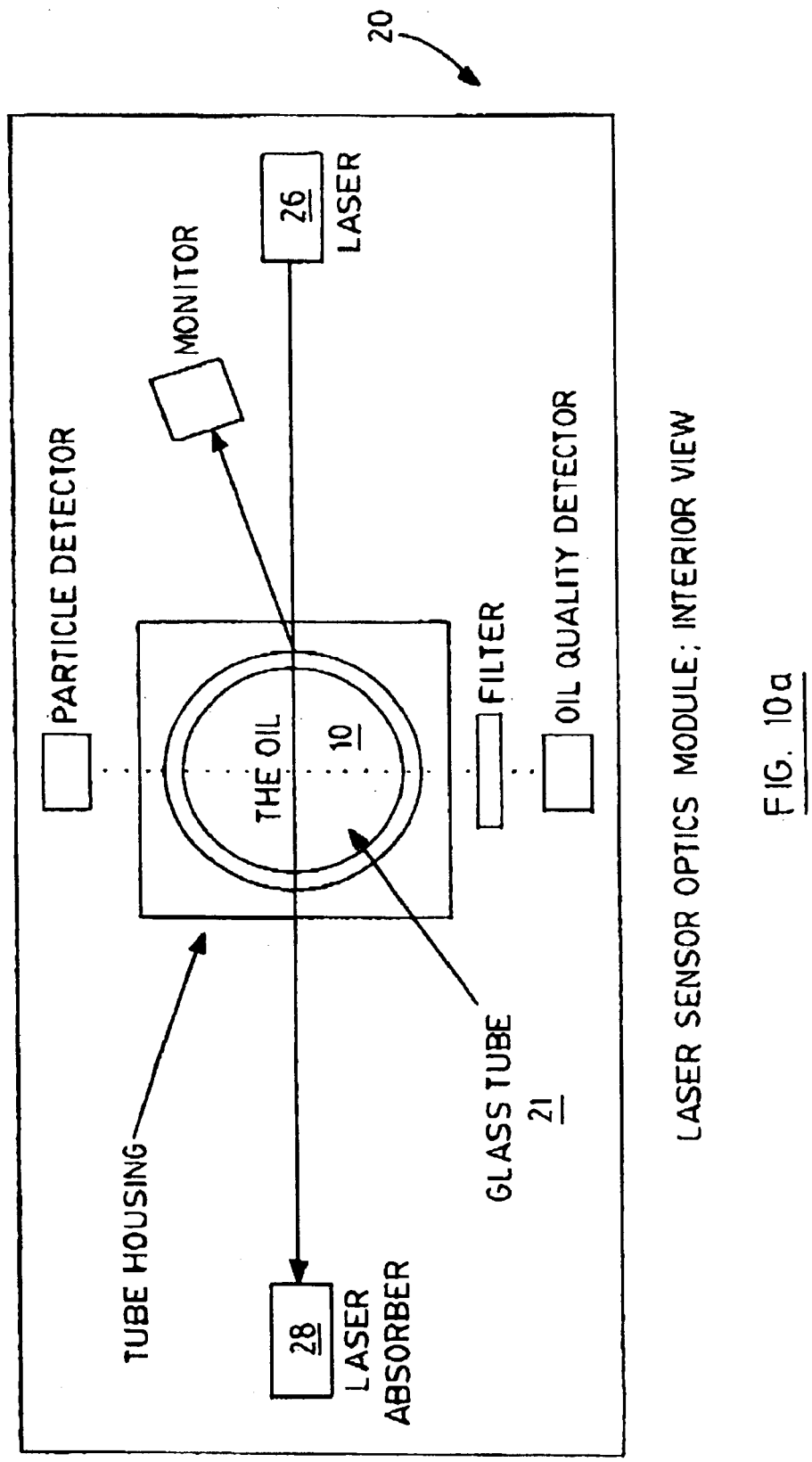
FIG. 10a illustrates schematically an interior view of the optical arrangement for the oil sensor in accordance with one embodiment of the invention.

Based on the experimental results an oil quality sensor device 20 (FIGS. 10a and 10b) was constructed and tested. The size of the unit 20 was 8.5"×4.25"×1.75", and power was supplied by a battery (not shown). Oil (10) testing was performed in a 1" diameter glass bottle or tube 21, and the oil quality measurement is displayed by LED bar graphs 22 (FIG. 10b) ranging in colour from green to red in ten steps. Separate bar graphs 22 are preferably provided for display of chemical quality of the oil (based on fluorescence) and for display of floating particle concentration in the oil (based on elastic light scattering). These are displayed after suitable electronic amplification of the signals. The amplifier gain calibration of the system is easily adjustable to the required level.

The development of the oil quality sensor device 20 involved the testing of various diode lasers, photo-detectors, optical filters, beam dumps, electronics and amplification systems as well as appropriate configuration. A choice of components was made on the basis of efficiency, sensitivity, and cost. The device 20 included a 635 nm diode laser 26, a silicon photodiode with an acceptance angle of more than 60 degrees, an appropriate "beam dump" or absorption chamber 28 to absorb the laser beam after it passes through the oil 10 that is being measured. Measurements of oil quality using the device 20 were compared and calibrated with the results of our laboratory testing described above. It was confirmed that the device 20 works as per design, displaying optical readouts on the LED 22, ranging from lighted green bars for good quality oil, yellow for medium quality oil, all the way up to red bars for over-used oil. The display panel 22 readout can be changed based on food industry standards, by adjusting the electronic amplifier gain inside the portable oil quality sensor.

Optionally, the unit 20 may be modified as shown in FIG. 10, so that the LED bar graph display can be mechanically separate from the main optical part, so that the total unit is made up of two modular units 40,42 interfaced by a cable 44. In this way, the mechanical position and orientation of the two modules 40,42 can be arranged for ease and convenience of operation. The prototype device 20 can work satisfactorily with two settings in order to determine oil quality for the four distinct foods. Accordingly, a two-position toggle switch 34 was installed to allow the user to switch the operation of the device from french fries and the other meat products. All of the oils 10 used for meat products can be measured using a single setting.

In regular use, operation is achieved by a push power button 32 and the two position food selector switch 34 to select oil testing for meats or french fries. The device 20 provides a visual indication to The restaurant manager whether the oil should be re-used or discarded. In addition, the device 20 provides chemical quality information instantaneously and independently of whether the oil 10 has or has not been finely filtered. Sample operational guide for the unit 20 is as follows:

SAMPLE OPERATION GUIDE

Oil Sensor and Measurement Protocol

1. Place the bottles in the wood rack slots and fill with filtered oil below the neck. No labels should be attached to the bottles.

2. Wait till the temperature drops to 50 degrees C. (thermometer supplied).

3. Wipe the bottle, clean off any spilled oil and insert into the sample port of the sensor. The sensor should be set flat on a table or counter top.

4. Set the 2-way chrome switch as follows:
   (a) for french fries the switch should be turned to the right (fr) position;
   (b) for all other foods the switch should be turned to the centre (mt) position.

5. Cover the bottle with the cap attached to the chain.

6. Push down the red "on" button for 2 seconds and on the "read" display note the number of bars that light up steadily. (There are a total of 10 bars; they are from the left, 5 green, 3 yellow and 2 red).

Figure 10B:
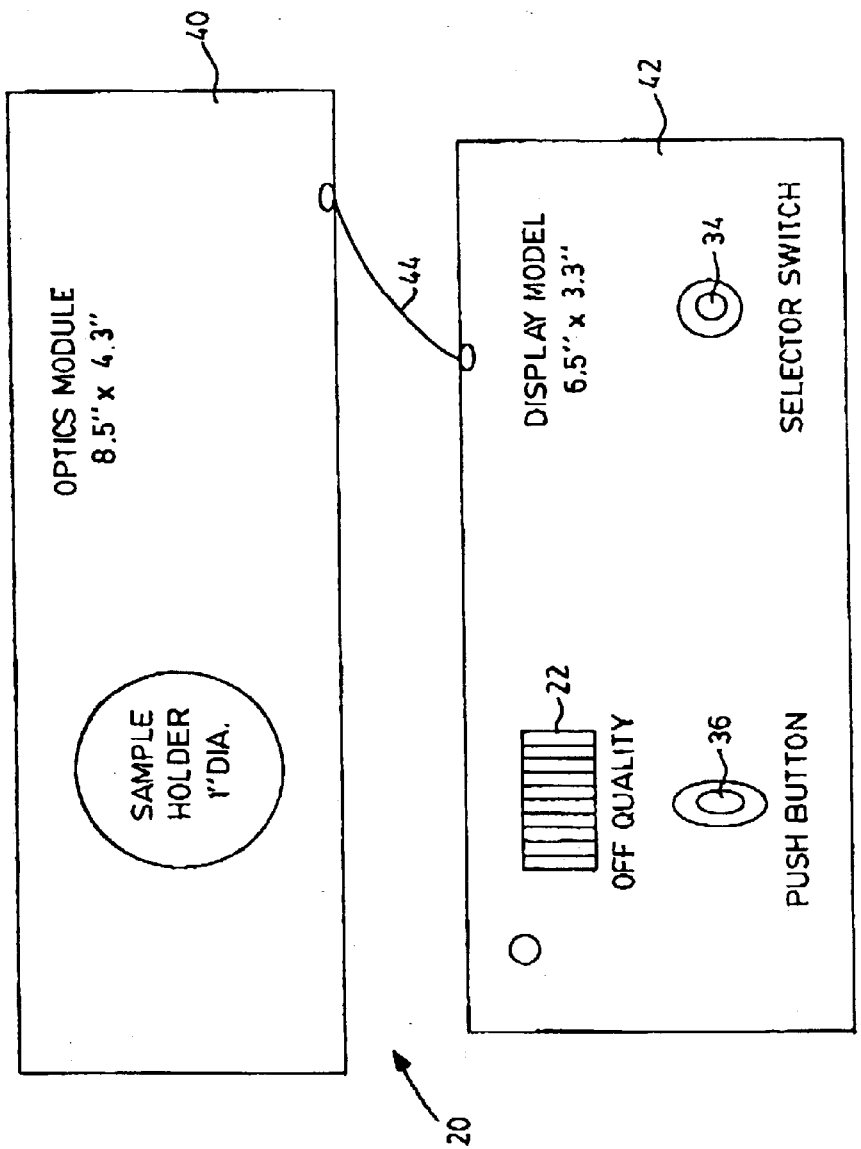
Figure 11:
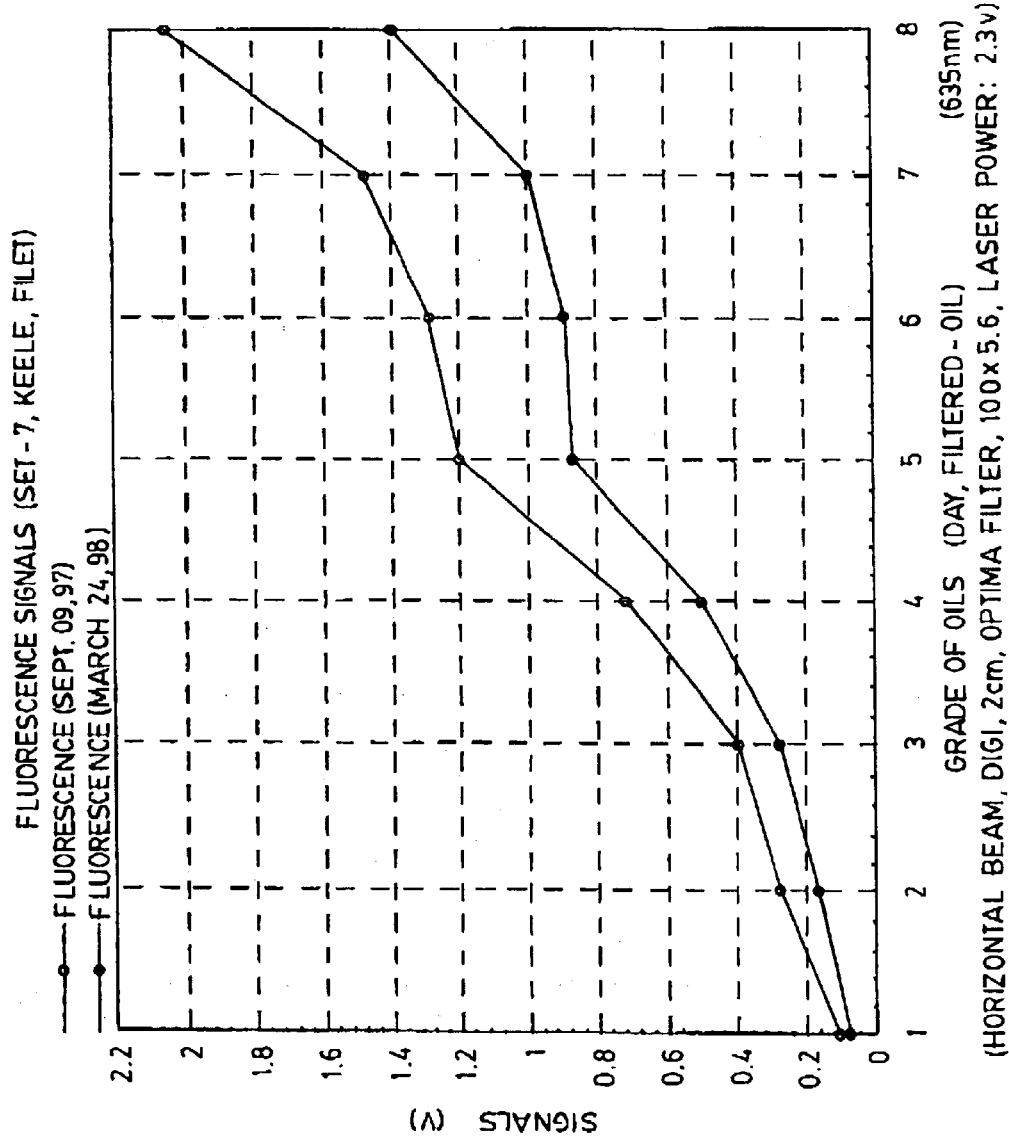
FIG. 11 illustrates graphically the variation in fluorescence for meat oil (filet) measured at a six month interval.
Figure 12A:
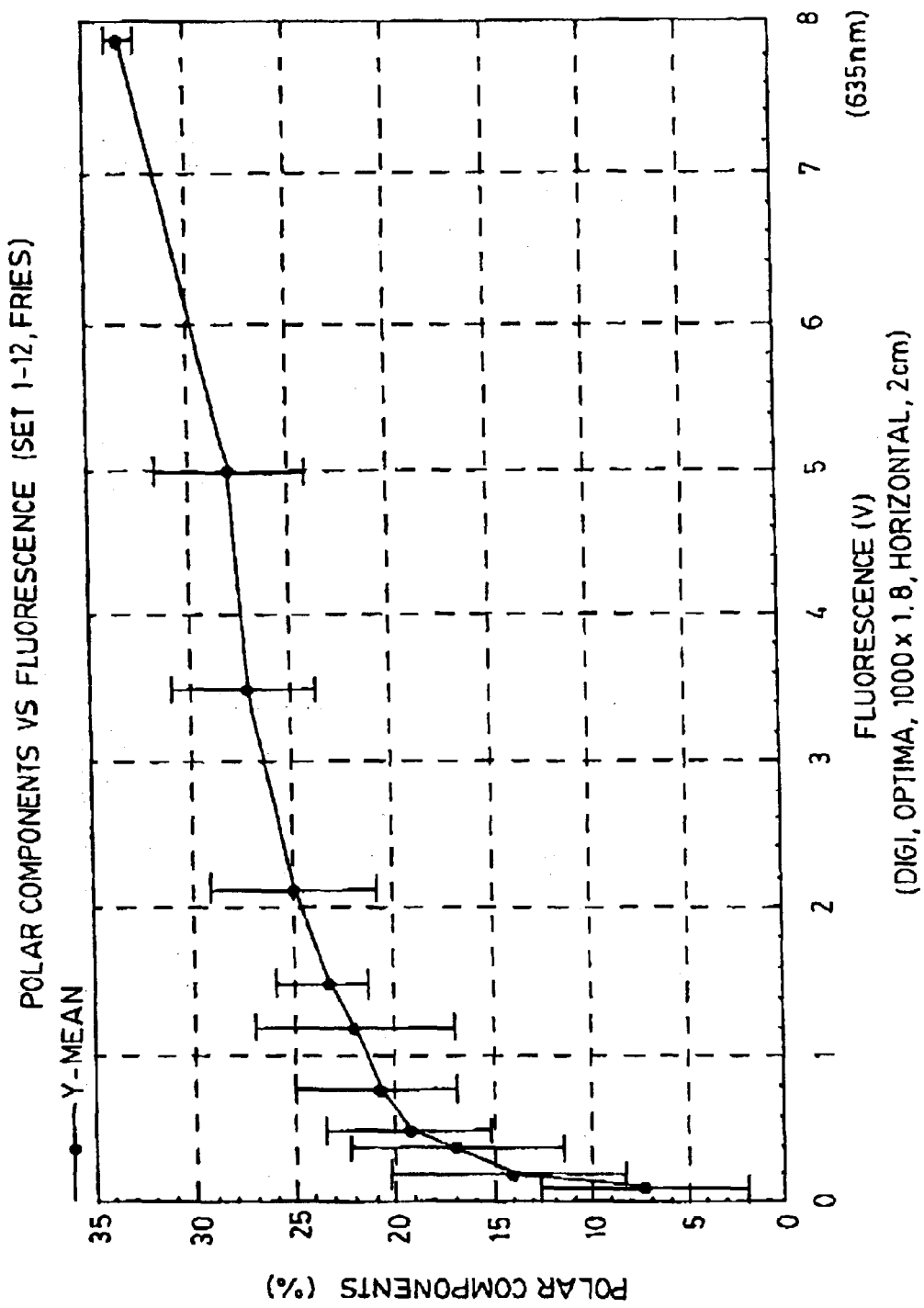
FIG. 12a illustrates a regression curve (polar components vs. fluorescence) for the average values of all the measurements of french fry oil (12 sets)
Figure 12B:
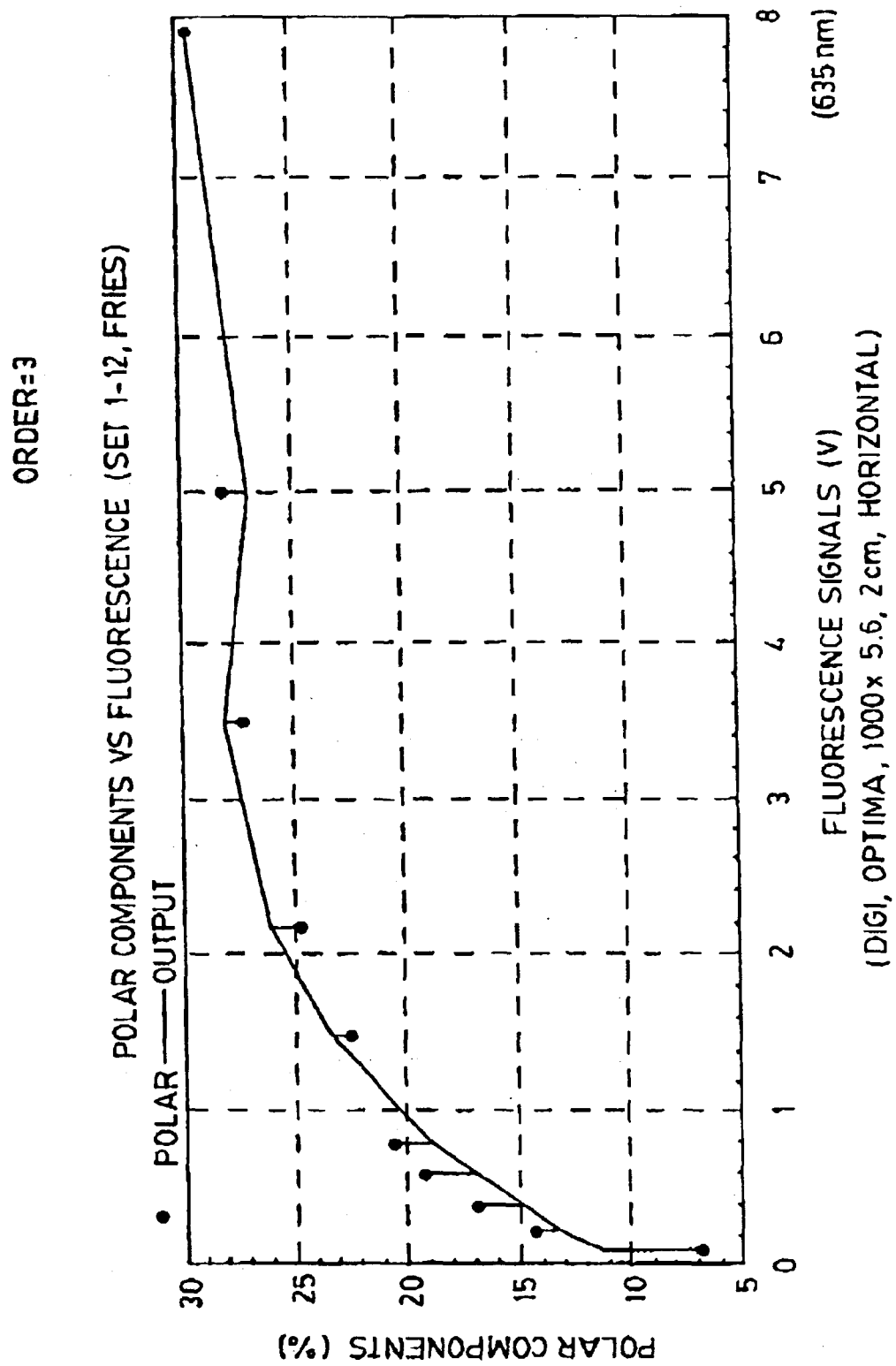
FIG. 12b illustrates a regression curve (best third order polynomial fit) for all the measurements of french fry oil (12 sets) wherein dots are used to indicate average values.
Figure 12C:
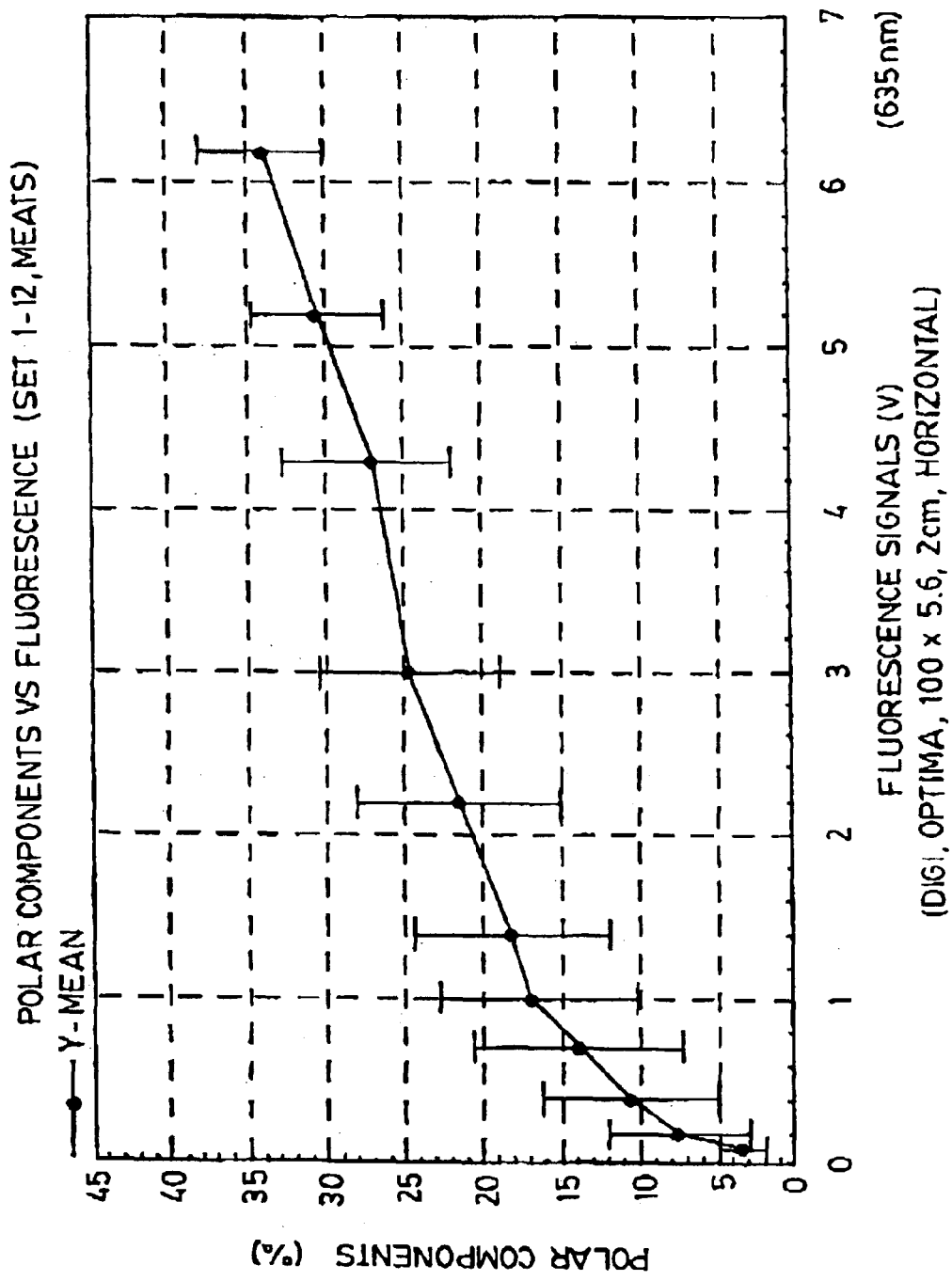
FIG. 12c illustrates a regression curve (polar components vs. fluorescence) for the average values of all the measurements of all three meat oils (12 sets).
Figure 12D:
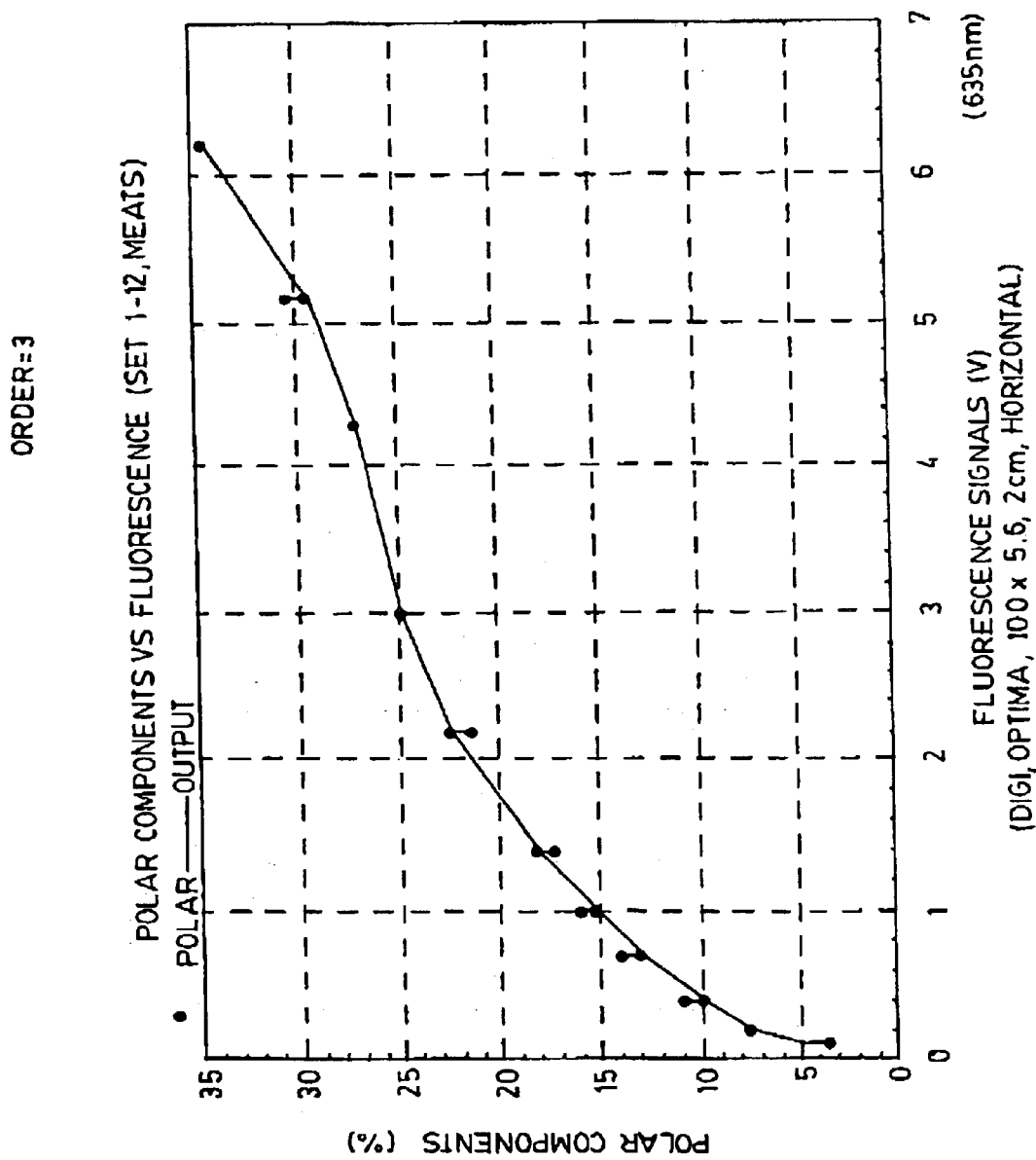
FIG. 12d illustrates a regression curve (best third order polynomial fit) for all the measurements of all three meat oils (12 sets) wherein dots are used to indicate average values.
Figure 12E:
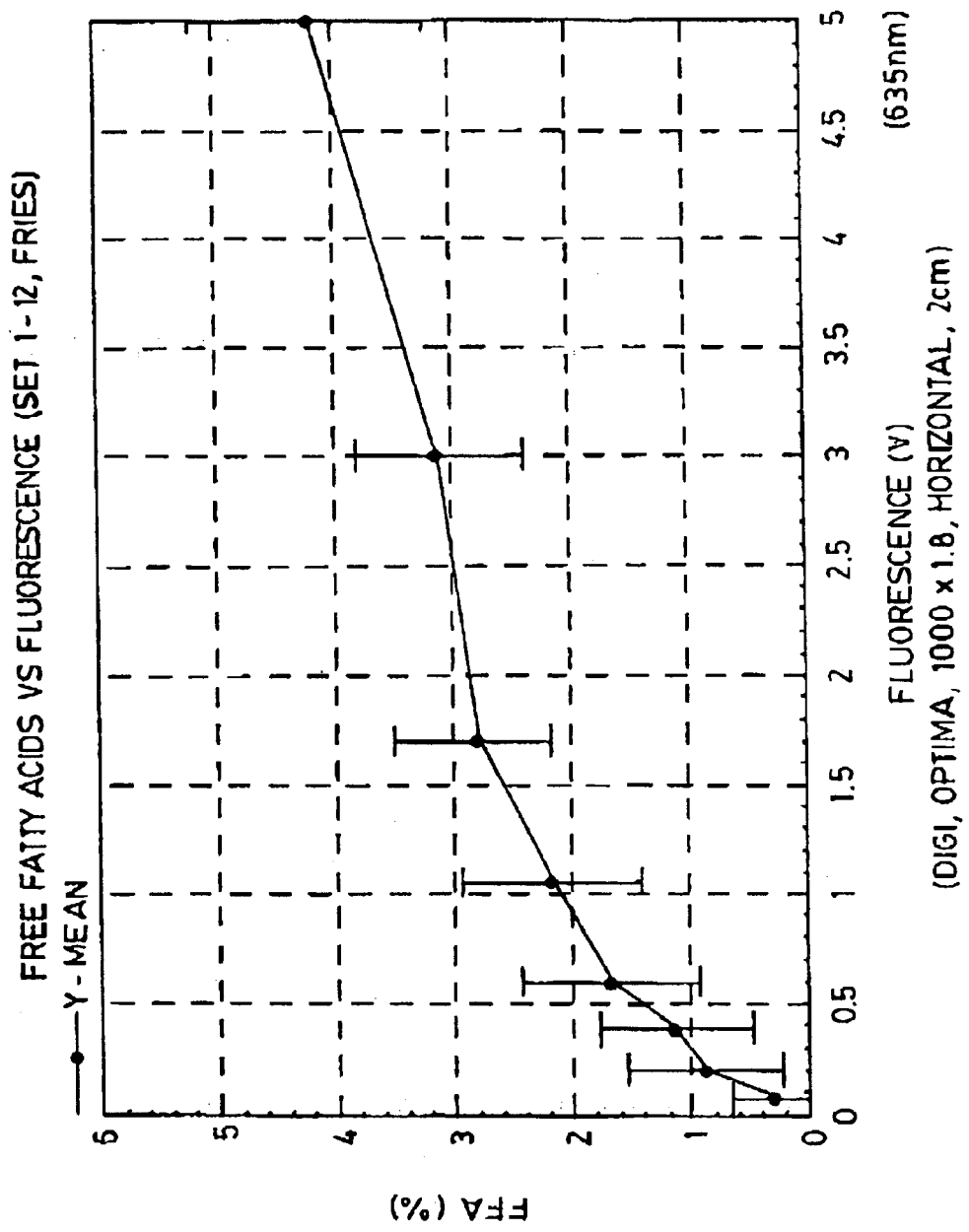
FIG. 12e illustrates graphically fatty acid percentage vs. fluorescence regression curve for french fries.

In an alternate embodiment, the unit 20 was also modified so that the LED bar graph display 22 could be mechanically separate from the main optical part. In this configuration, the total unit 20 is made up of two modular units 40,42 interfaced by one or more cables 44 (FIG. 10b). In this way, the mechanical position and orientation of the two modules 40,42 can be arranged for ease and convenience of operation The regression curves for all of the samples together are shown in FIGS. 12a–d. FIGS. 12a and b include all the measurements of the french fries from 12 sets of oil samples and show curves with standard deviations and a regression curve of the average values. The standard deviation about the average value is depicted as a vertical bar. FIGS. 12c and d include all the three meats from all the 12 sets. FIGS. 12a and 12c are regression curves showing standard deviations. FIGS. 12b and 12d are best fits for the average value of the fluorescence plotted against the polar compound value from chemical measurements. Since the fluorescence data showed reasonably good correlation with respect to both polar compounds and fatty acid, analysis was limited to the relationship between fluorescence and polar compounds. FIG. 12e shows the fatty acid regression curve for french fries. As pointed out earlier, these curves are obtained using a least squares fit to the data and the standard deviation is determined.

(d) Development of a Built-In System

Figure 13:
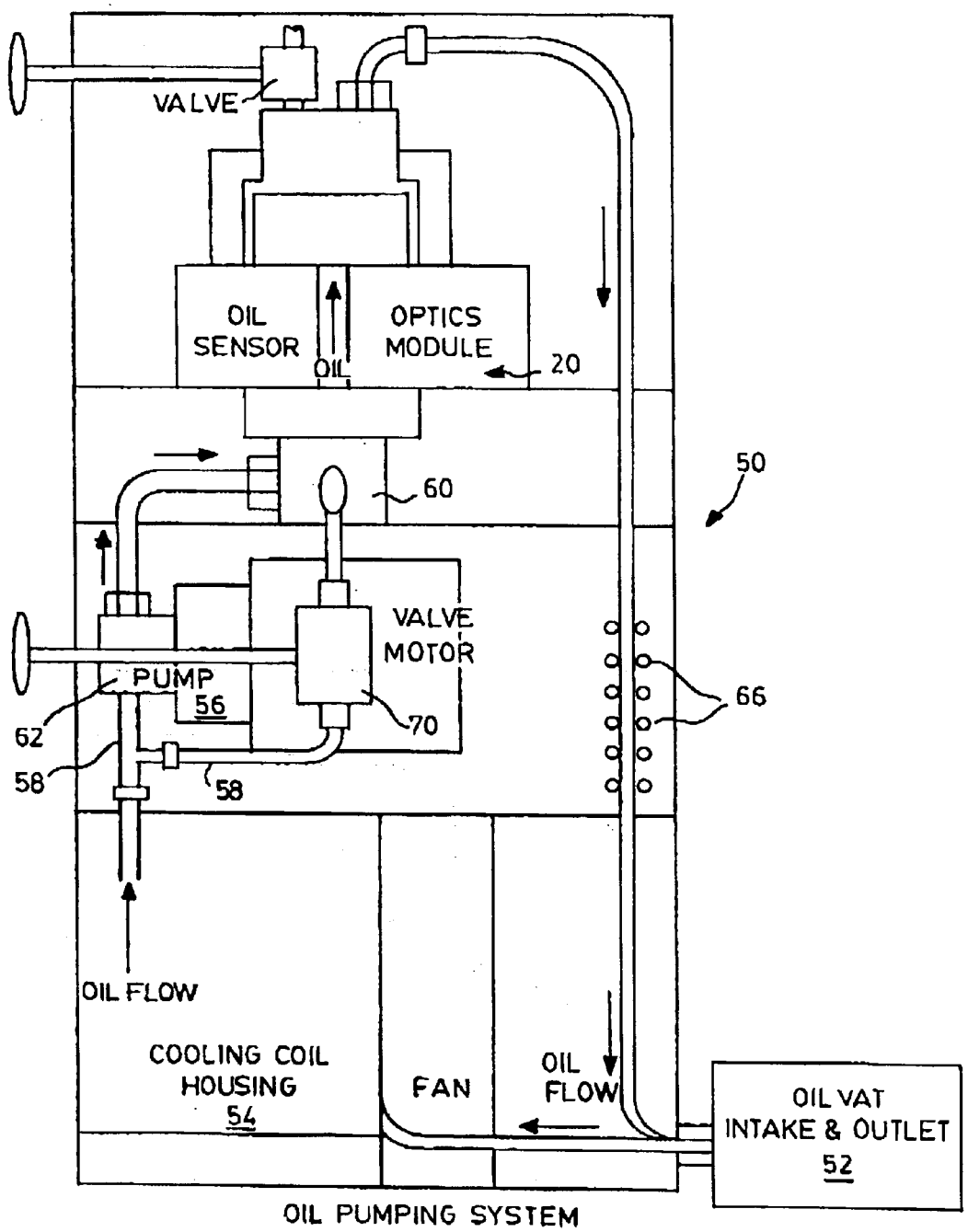
FIG. 13 illustrates schematically an oil pumping system.

On the basis of field tests of the portable units 10, it is envisioned that a permanent built-in unit 50 (FIG. 13a) could be developed so that oil from a hot oil vat 52 could be pumped through the unit and circulated continuously. Most preferably, the built-in unit 50 does not require manual transfer of oil from the cooking vats 52 to the optical sensor device 20.

It has been determined that an appropriate cooling system is provided within the unit 50 to cool the hot oil from the hot oil vat temperature of about 175 C. to a measuring temperature of about 60 C. This cooling system 54 includes a pump 56 adapted to handle high temperatures, and a heating and plumbing system which prevents the oil from freezing in the line at any stage of start up and shut down of the unit 50. The pump 56 is most preferably food compatible (such as a Micro Pump™ model 185T) and most preferably has Teflon™ or stainless steel gears.

The oil is pumped back into the vat 52 in a continuous loop. The oil flow rate at this setting is about 60 ml per minute. A filter 62 (FIG. 13a) is positioned in the plumbing line at the oil intake for the protection of the pump 56. Oil entering the system is pre-filtered at least to the quality of the filter paper normally used at MacDonalds.

Heating tapes 66 are incorporated in the plumbing lines 58 to prevent oil freeze-up during start up and shut down of the unit 50. In addition thermal switches are also incorporated to protect the pump 62 and components from overheating. A lower system valve 70 controls a line that bypasses the pump 62 during shut down and the upper valve opens to the atmosphere during shut down.

Hot oil drawn from the hot oil vat 52 is initially air cooled in a stainless steel coil 54. Fine tuning of the oil temperature at the oil sensor port in accomplished by thermocouple sensing of the temperature which is fed back to a control circuit which controls the pump 56 speed. Sample operating instructions for the built-in unit 50 are as follows:

SAMPLE OPERATING INSTRUCTIONS

Operating Instructions

START UP

1. Turn the Power switch ON, located at the right side of the Unit. (The oil should be at about the frying temperature before start up).

2. Turn both black knobs on the left side of the Unit fully in the clock-wise direction (only finger-tight snug).

3. Push the START button on the Power Bay. (The red START light and the pilot light on the right side bottom of the Unit come on). Cooling fan in the Unit comes on in about 5 min. and the pump starts shortly after. The system stabilizes in about 20 min.).

SHUT DOWN

1. Push STOP button on the Power Box; oil should be at frying temperature. (Green light comes on and the red START light goes off).

2. Turn both black knobs on the left side of the Unit fully in the counterclockwise direction.

After about 25 min. the red START light comes on again (now both the green and red lights are on at the Power Box). The red light indicates power now goes to the Unit for the hearing tape. After about 3 min. both the red and green lights on the Power Box go out. The SHUT DOWN phase of the Unit is now complete.

3. After the green and red lights go out on the Power Box, then turn the Power switch on the right side of the Unit to the OFF position.

OIL QUALITY MEASUREMENT

1. Set the selector switch on The front panel to either Meat or Fries as required (Meat, for all meats and Fries, for French Fry).

2. Press and hold the push button on the front panel to read OIL QUALITY.

If a red circular light at the top left of the front panel stays on consistently when the oil quality button is pushed down before start-up or after shut-down, it may indicate a drop in laser power. If this happens for several days servicing may be required.

While the description describes use of the apparatus in the evaluation of cooling oil, the invention is not so limited. If desired, the apparatus could equally be used to evaluate the qualities of other oils, including by way of non-limiting example motor and industrial oils and lubricants or other liquids which may be subject to degradation and chemical change. While the same principles may apply to other oils, a careful recalibration of the device is required in order for it to provide useful information in these cases.

Therefore what is claimed:

1. A device for monitoring the quality of oil comprising:
   (a) a laser for illuminating oil with laser light;
   (b) an optical filter allowing fluorescent light scattered by said oil to pass through said optical filter;
   (c) a first photodetector for detecting the fluorescent light that has passed through said optical filter; and
   (d) an electronic display for displaying an indicator of a correlation between said fluorescent light detected by said first photodetector and the quality of said oil, said electronic display calibrated to a type of oil.

2. The device of claim 1 further comprising a laser dump for trapping said laser light transmitted directly through said oil.

3. The device of claim 1 further comprising a second photodetector, said second photodetector, simultaneously and independently of said first photodetector, detecting laser light scattered by suspended solid particles in said oil.

4. The device of claim 3 wherein said electronic display displays an indicator of at least one of: the oil should be discarded; the oil should be filtered and re-used; and the oil should be re-used for a specified purpose.

5. The device of claim 1 wherein said oil comprises cooking oil and wherein substantially only fluorescent light scattered by said oil is allowed to pass through said optical filter.

6. The device of claim 1 wherein said electronic display displays an indicator indicative of an oil degraded condition when said correlation indicates a polar component fraction of said oil exceeds approximately 25%.

7. The device of claim 1 wherein said correlation is performed by a computer and wherein said computer is adapted to be re-calibrated for at least one of differing oil conditions and differing oil usage conditions.

8. The device of claim 1 comprising at least one portable unit, said at least one portable unit adapted to receive oil at a specified temperature.

9. The device of claim 8 wherein said at least one portable unit is adapted to receive oil continuously through operation of a pumping system.

10. The device of claim 1 comprising a calibration for a plurality of oil types, said device adapted to switch from one calibration to another.

11. The device of claim 10 wherein a calibration for one of said plurality of oil types comprises a set of values indicative of the degradation of said one of plurality of oil types.

12. A method of measuring the quality of oil comprising:
    (a) illuminating oil with laser light; and
    (b) displaying an indicator of a correlation between detected fluorescent light scattered by said oil illuminated by said light and the quality of said oil.

13. The method of claim 12 further comprising trapping said laser light transmitted directly through said oil.

14. The method of claim 12 further comprising prior to displaying:
    (a) filtering fluorescent light scattered by said oil, and
    (b) detecting said filtered fluorescent light.

15. The method of claim 13 further comprising simultaneously and independently of said detecting said filtered fluorescent light, detecting laser light scattered by suspended solid particles in said oil.

16. The method of claim 14 wherein said displaying comprises displaying an indicator of at least one of: the oil should be discarded; the oil should be filtered and re-used; and the oil should be re-used for a specified purpose.

17. The method of claim 13 wherein said displaying comprises displaying an indicator indicative of an oil degraded condition when said correlation indicates a polar component fraction of said oil exceeds approximately 25%.

18. The method of claim 13 further comprising receiving oil at a specified temperature.

19. The method of claim 18 wherein receiving comprises receiving oil continuously through operation of a pumping system.

20. The method of claim 13 further comprising calibrating said correlation for a plurality of oil types and wherein said correlation is adapted to switch from one calibration to another.

* * * * *